United States Patent [19]
O'Dwyer

[11] Patent Number: 5,928,157
[45] Date of Patent: *Jul. 27, 1999

[54] APNEA DETECTION MONITOR WITH REMOTE RECEIVER

[76] Inventor: Joseph E. O'Dwyer, 149 Old York Rd., Ringoes, N.J. 08551-1802

[ * ] Notice: This patent is subject to a terminal disclaimer.

[21] Appl. No.: 09/012,023

[22] Filed: Jan. 22, 1998

[51] Int. Cl.$^6$ ..................................................... A61N 5/00
[52] U.S. Cl. ........................................... 600/534; 600/532
[58] Field of Search ..................................... 600/534, 528

[56] References Cited

U.S. PATENT DOCUMENTS

| | | |
|---|---|---|
| D. 353,202 | 12/1994 | Hong . |
| 4,657,026 | 4/1987 | Tagg . |
| 4,909,260 | 3/1990 | Salem et al. . |
| 5,107,855 | 4/1992 | Harrington et al. . |
| 5,241,300 | 8/1993 | Buschmann . |
| 5,295,490 | 3/1994 | Dodakian . |
| 5,615,688 | 4/1997 | O'Dwyer . |

Primary Examiner—Robert L. Nasser
Assistant Examiner—Michael Astorino
Attorney, Agent, or Firm—Kenneth P. Glynn, Esq.

[57] ABSTRACT

The present invention is an apnea detection device with a remote monitoring capability. It includes a transmitter housing having a first portion and a second portion, the first portion has a structure with a bottom planar extension which has a stop coupled thereto and extended upwardly therefrom. The second portion of the housing is adapted to be slidably inserted within the interior space of the first portion. There is also a stiff two piece strap with ends connected to the first portion of the housing and second portion of the housing and a fastener, whereby the strap allows securement to a chest of an infant. There is a conductive strip and a plurality of linearly aligned contacts whereby a decreasing amount of contacts are connected via the conductive strip upon the sliding of the second portion of the housing from an unbiased orientation to a biased orientation. Upon detection by the comparator of the strip connecting an amount of contacts less than a predetermined amount a transmitter sends a signal to a remote receiver which emits an alarm.

14 Claims, 3 Drawing Sheets

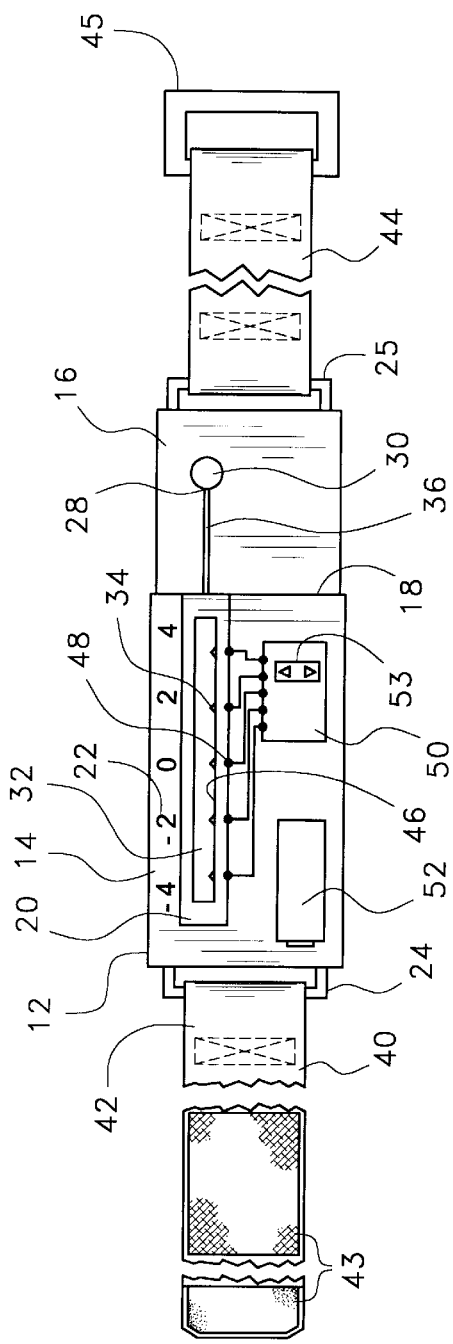
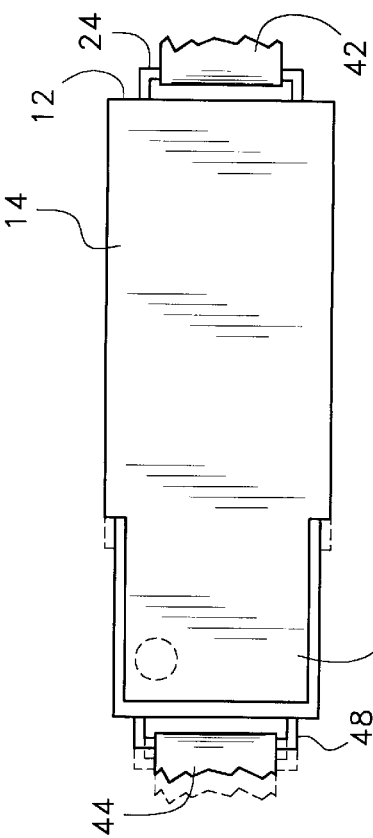
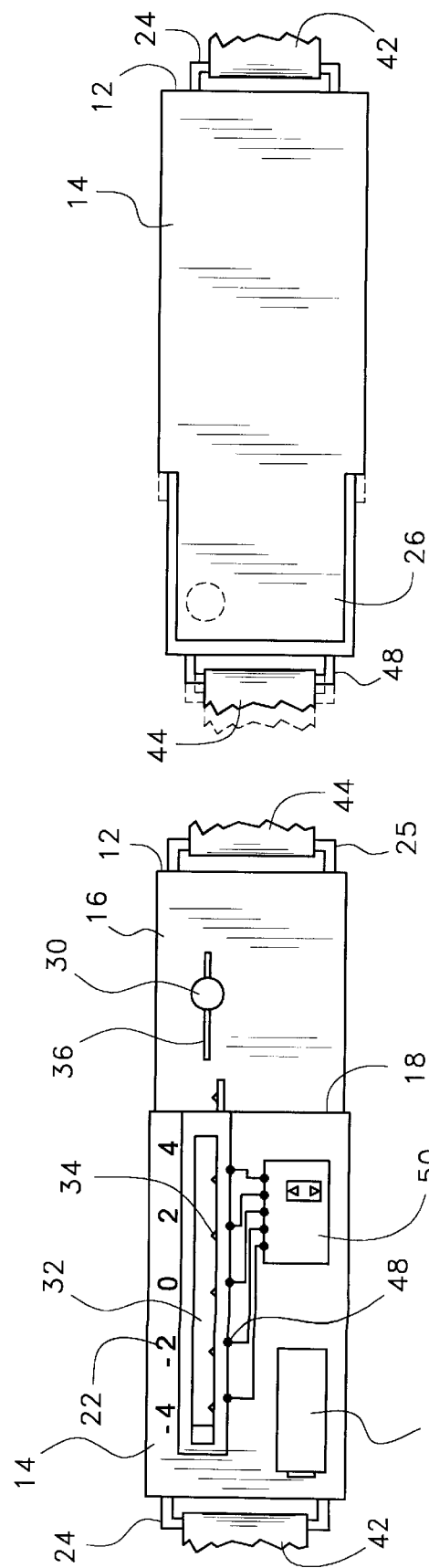
Fig. 3
Fig. 5
Fig. 4

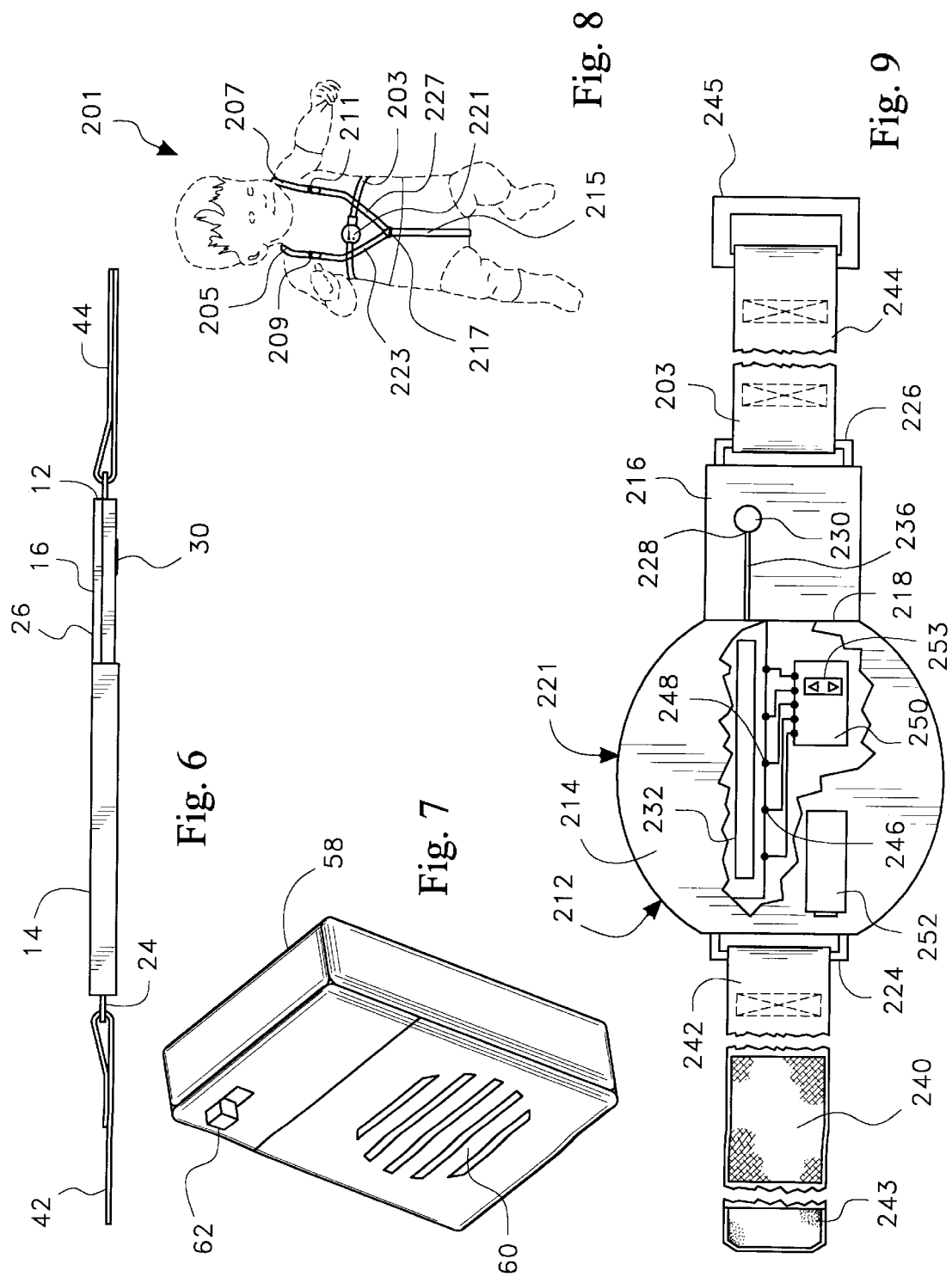

APNEA DETECTION MONITOR WITH REMOTE RECEIVER

REFERENCE TO RELATED CASES—INCORPORATION BY REFERENCE

The present invention is an expanded version of the invention set forth in U.S. Pat. No. 5,615,688 by the same inventor herein issued on Apr. 1, 1997 and incorporated herein in its entirety by reference.

BACKGROUND OF THE INVENTION

1. Field of the Invention

The present invention relates to an apnea detection device with a remote monitor and more particularly pertains to preventing the death of an infant due to an illness such as SIDS with an associated remote monitor. It may also be used to prevent the death of individuals having respiratory difficulties of any age, such as people with acute emphysema, acute asthma and Duchesne's disease.

2. Information Disclosure Statement

The use of apnea prevention devices is known in the prior art. More specifically, apnea prevention devices heretofore devised and utilized for the purpose of preventing the death of an individual are known but operate in a more complex fashion or in a different manner from the present invention. The following patents are representative of the art:

U.S. Pat. No. 5,295,490 to Dodakian describes a self-contained apnea monitor of the invention detects an apnea event or shallow breathing in a patient such as an infant, and generates an audible and visual alarm in response thereto. The monitor includes an elastic fabric belt for snugly encircling the abdomen or chest of an infant and a detector unit for detecting expansion or contraction of the elastic fabric belt caused by respiration. To this end, the belt includes a helical spring extending along its length. An inextensible wire is provided within the spring connecting a remote end of the spring to the detector unit. Thus configured, respiration of the infant causes the wire to be withdrawn from the detector unit. Within the detector unit, the wire is mounted to a recoil spring assembly which provides a biasing force for recoiling the wire subsequent to respiration. A detecting arm or magnet is mounted to a barrel containing the recoil spring within an electrical circuit provided to detect motion of the detecting arm or magnet. The electrical circuit measure s a time interval between consecutive respirations and generates an audible alarm if the time interval exceeds a predetermined period of time.

U.S. Pat. No. 5,241,300 to Buschmann a transilluminated optical fiber is placed adjacent to an infant's respiratory moving parts using an elastic fabric. Use is made of the effect that moving the fiber causes a modulation of the intensity of the transmitted light to monitor the infant's breathing pattern to avoid S(udden) I(nfant) D(eath) S(yndrome).

U.S. Pat. No. 5,107,855 to Harrington et al describes an apnea monitor which detects breathing movement by a strap attached around the thorax region of the patient together with a Hall effect detector which is arranged to detect expansion movements of the body of the patient. The detector includes a first part mounted on one part of the strap and a transducer element attached to a second part of the strap so as to be pulled away from the first part against the bias of a spring and released toward the first part in dependence upon the movement. The position of the transducer element relative to the first part is transmitted wirelessly to a receiver using an antenna mounted on the bed frame construction. The signals are decoded to produce a series of values each dependent upon an instantaneous position of the transducer element. The values are monitored to detect increasing and decreasing values indicative of an aperiodic sinusoidal pattern associated with breathing.

U.S. Pat. No. 4,909,260 to Salem et al describes a portable belt-type monitor of body functions such as the heart and breathing is described formed of a plurality of articulated, distributed modules containing EKG sensors, a respiration sensor, circuitry including a microprocessor for sensing alarm conditions, a transmitter for sending alarm conditions to a remote receiver and a battery to drive the various circuits. A respiration sensor is described wherein tension changes in the belt due to breathing are transformed into opposing forces directed transversely to the belt and which cooperate to produce a reliable, sensitive detection of respiratory activities. The belt can be conveniently worn with reliable EKG sensing during normal body activities. A processor program is described whereby these body functions are monitored with alarm being generated when these functions exceed preset limits while preserving sufficient functional performance data when an alarm occurs.

U.S. Pat. No. 4,657,026 to Tagg describes an apnea alarm apparatus which detects the cessation of breathing of a human by monitoring movement of the ribcage by sensor means. The sensor means are connected to a summing amplifier which provides an electrical signal indicative of the breathing movement of the ribcage and upon a change in successive electrical signals, which indicates apnea, an alarm is activated.

U.S. Pat. No. Des. 353,202 to Hong describes an ornamental design for an abdominal breathing band.

In this respect, the apnea detection device with a remote monitor according to the present invention substantially departs from the conventional concepts and designs of the prior art, and in so doing provides an apparatus primarily developed for the purpose of preventing the death of an infant, senior citizen or any ailing individual due to an illness such as SIDS with an associated remote monitor.

Therefore, it can be appreciated that there exists a continuing need for a new and improved apnea detection device with a remote monitor which can be used for preventing the death of an infant due to an illness such as SIDS or other respiratory ailments with an associated remote monitor. In this regard, the present invention substantially fulfills this need.

Notwithstanding the prior art, the present invention is neither taught nor rendered obvious thereby.

SUMMARY OF THE INVENTION

The present invention is an apnea detection device with a remote monitoring capability. It includes a transmitter housing having a first portion and a second portion, the first portion has a structure, a top face, a bottom face, and an open side face, and a bottom planar extension integrally formed with the bottom face and extended outwardly therefrom within a plane in which the bottom face resides. The bottom planar extension includes a stop coupled thereto and extended upwardly therefrom, the second portion of the housing is adapted to be slidably inserted within the interior space of the first portion, wherein the second portion has an unbiased contracted orientation with the second portion proximally situated with respect to the first portion and a biased extended orientation with the second portion distally situated with respect to the first portion. There is also a stiff two piece strap with ends connected to the first portion of the housing and the second portion of the housing and a fastener, whereby the strap allows securement of the housing to a chest of an infant.

There is a conductive strip situated on the top planar extension of the second portion of the housing, and a plurality of linearly aligned contact situated within the interior space of the first portion of the housing, whereby a decreasing amount of contacts are connected via the conductive strip upon the sliding of the second portion of the housing from an unbiased orientation to a biased orientation. There is a transmitter subunit situated within the first portion of the housing and connected to a small battery and the contacts, the transmitter subunit including a comparator which is adapted to monitor the conductivity between subsequent contacts and a transmitter adapted to transmit an activation signal upon the detection by said comparator of the strip connecting an amount of contacts less than a predetermined amount. There is at least one remote receiver including a housing with a speaker adapted to emit an alarm upon the actuation thereof, a power source and a receiver unit adapted to actuate the speaker upon the receipt of the activation signal via the transmitter unit.

BRIEF DESCRIPTION OF THE DRAWINGS

The present invention should be more fully understood when the specification herein is taken in conjunction with the drawings appended hereto wherein:

FIG. 3 is a front elevational view of the present invention;

FIG. 4 is a cut away view of the transmitter housing of the present invention;

FIG. 5 is a rear elevational view of the transmitter housing of the present invention;

FIG. 6 is a side plan view of the transmitter housing of the present invention;

FIG. 7 is a perspective view of the receiver employed in the present invention;

FIG. 8 shows another perspective illustration with an infant of another preferred embodiment of an apnea detection device of the present invention; and, FIG. 9 shows a detailed, partial, front view of the device itself which is shown in FIG. 8.

Similar reference characters refer to similar parts throughout the several views of the drawings.

DETAILED DESCRIPTION OF THE PRESENT INVENTION

Figures 1, 2:
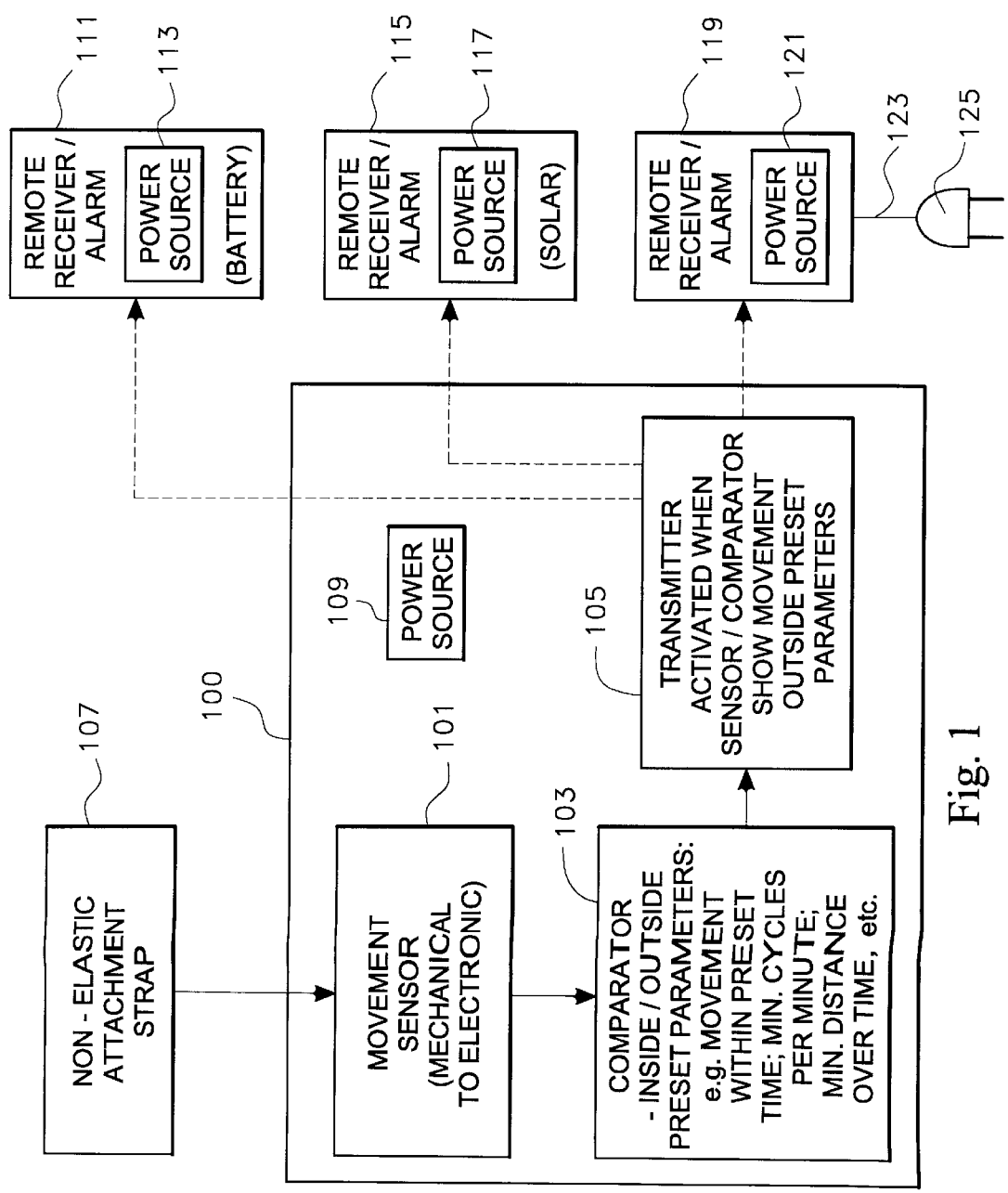
FIG. 1 is a schematic overview diagram of a present invention apnea detection device.
FIG. 2 is a perspective illustration of one preferred embodiment of the apnea detection device with a remote monitor constructed in accordance with the principles of the present invention.

In view of the foregoing disadvantages described in the Information Disclosure Statement above which are inherent in the known types of prior art apnea prevention devices, the present invention provides an improved apnea detection device with a remote monitor. As such, the general purpose of the present invention, which will be described subsequently in greater detail, is to provide a new and improved apnea detection device with a remote monitor which has all the advantages of the prior art and none of the disadvantages. While the word "apnea" is used throughout this application, it should be construed broadly to include all illnesses which involve respiratory difficulties where significantly decreased breathing or cessation of breathing may occur, including, but not limited to, emphysema, acute asthma, Duchesne's Disease; heart ailments, etc. FIG. 1 schematically illustrates the essential features of the present invention apnea detection device. Large block 100 represents a first component which includes a motion sensor 101 with means for converting mechanical motion into electronic signals, a comparator 103 which relies upon comparison of actual movement of the mechanical aspects of the movement sensor with predetermined parameters, a transmitter 105 for transmission to one or more receivers and a power source 109. First component 100 is attached to a nonelastic strap 107 which attaches to the chest of an infant such as is illustrated in FIG. 2. By the expansion and contraction movement of the lungs of the infant, the movement sensor will send electronic signals to a comparator. As long as the infant is breathing normally, actual movement within will be accepted in predetermined parameters. When breathing is acutely abnormal or ceases, movement will be outside of those parameters and transmitter 105 will transmit a signal to one or more remote receiver/alarm such as remote receiver/alarm 111, 115 and 119. Each of these have power sources and may be battery operated, solar operated or any other power arrangement. For example, remote receiver/alarm 111 might have power source 113 as a battery power source with one or more batteries and remote receiver/alarm 115 may have a solar power source 117 and remote receiver/alarm 119 might have a power source 121, which includes an electric line 123 with plug 125 adapted for household current.

To attain this, the present invention, in one embodiment, essentially comprises a transmitter housing with a generally rectangular configuration. As best shown in FIGS. 2 and 3, the transmitter housing has a first portion and a second portion. The first portion includes a top face, a bottom face, and a thin periphery formed therebetween thus defining an interior space. Access is afforded to the interior space via an open side face. The first portion further includes a transparent window formed on the top face with indicia printed adjacent thereto. A closed coupling loop is formed on a side face of the housing opposite the open side face. A bottom planar extension is integrally formed with the bottom face and extended outwardly therefrom. The bottom planar extension resides within a plane in which the bottom face resides. The bottom planar extension includes a post coupled thereto. The post extends upwardly therefrom with a bulb formed on a top portion thereof. With reference still to FIGS. 2 and 3, the second portion of the housing includes a top face with a periphery integrally coupled thereto and depending therefrom. The second portion further includes a top planar extension integrally formed with the top face thereof. The top planar extension is adapted to be slidably inserted within the interior space of the first portion. A plurality of markers are printed on the top planar extension which are visible through the window of the first portion. As such, the markers work in conjunction with the indicia of the first portion for indicating a depth in which the top planar extension is inserted within the first portion. The second portion further includes a groove formed in the top surface thereof for accepting the post therein. Such a feature maintains a slidable relationship between the first portion and second portion. Also, another closed coupling loop is integrally coupled to the periphery of the second portion opposite the top planar extension thereof. The second portion has an unbiased contracted orientation with the second portion proximally situated with respect to the first portion. The second portion also has a biased extended orientation with the second portion distally situated with respect to the first portion. Also included is a stiff strap with a first extent having a first end coupled to the coupling loop of the first portion of the housing. A second end of the first extent has a pair of pile fasteners coupled thereto. The strap further has a second extent with a first end coupled to the coupling loop of the second portion of the housing. A second end of the second extent has a buckle coupled thereto. The strap thus allows the securement of the transmitter housing to a chest of an infant for allowing the housing to be repeatedly biased coincidently with the breathing of the infant. A conductive strip is situated on the top planar extension of the second portion of the housing. Working in conjunction with the strip is a plurality of linearly aligned contacts. The contacts are situated within the interior space of the first portion of the housing in linear alignment and in contact with the conductive strip. In operation, a decreasing amount of contacts are connected via the conductive strip upon the sliding of the second portion of the housing from an unbiased orientation to a biased orientation. Further included is a transmitter unit situated within the interior space of the first portion of the housing. The transmitter subunit is connected to a small battery and the contacts. The transmitter subunit includes a comparator which is adapted to monitor the conductivity between subsequent contacts. Also, the transmitter subunit has a transmitter which is adapted to transmit an activation signal upon the detection by the comparator of the strip connecting an amount of contacts greater than a predetermined amount for a predetermined amount of time. Finally, as shown in FIG. 7, a receiver includes a housing with a generally rectangular configuration. A speaker located within the receiver housing is adapted to emit an alarm upon the actuation thereof. A receiver unit also situated within the receiver housing is adapted to actuate the speaker upon the receipt of the activation signal via the transmitter unit.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved apnea detection device with a remote monitor which has all the advantages of the prior art apnea prevention devices and none of the disadvantages.

It is another object of the present invention to provide a new and improved apnea detection device with a remote monitor which may be easily and efficiently manufactured and marketed.

It is a further object of the present invention to provide a new and improved apnea detection device with a remote monitor which is of a durable and reliable construction.

An even further object of the present invention is to provide a new and improved apnea detection device with a remote monitor which is susceptible of a low cost of manufacture with regard to both materials and labor, and which accordingly is then susceptible of low prices of sale to the consuming public, thereby making such apnea detection device with a remote monitor economically available to the buying public.

Still yet another object of the present invention is to provide a new and improved apnea detection device with a remote monitor which provides in the apparatuses and methods of the prior art some of the advantages thereof, while simultaneously overcoming some of the disadvantages normally associated therewith.

Still another object of the present invention is to prevent the death of an infant due to an illness such as SIDS.

Lastly, it is an object of the present invention to provide a new and improved apnea detection device with a remote monitor comprising a transmitter housing having a first portion and a second portion. The second portion has an unbiased contracted orientation with the second portion proximally situated with respect to the first portion. The second portion also has a biased extended orientation with the second portion distally situated with respect to the first portion. Also included is a strap for allowing the securement of the housing to a chest of an infant thus allowing the housing to be repeatedly biased coincidently with the breathing of the infant. A detection mechanism is included with the transmitter housing for monitoring biasing of the second portion associated with the respiration of the infant. Further included is a transmitter unit situated within the interior space of the first portion of the housing and connected to a small battery and the detection mechanism. The transmitter unit is adapted to transmit an activation signal upon the detection via the detection mechanism of an anomaly in the respiration of the infant. Finally, a receiver includes an alarm adapted to emit an audible signal upon the actuation thereof and a receiver unit adapted to actuate the alarm upon the receipt of the activation signal via the transmitter unit.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

With reference now in particular to FIG. 2, a new and improved apnea detection device with a remote monitor embodying the principles and concepts of the present invention and generally designated by the reference numeral 10 will be described.

The present invention, the new and improved apnea detection device with a remote monitor, is comprised of a plurality of components. Such components in their broadest context include a transmitter housing, strap, conductive strip, contacts, transmitter and receiver. Such components are individually configured and correlated with respect to each other so as to attain the desired objective.

More specifically, it will be noted that the device 10 of the present invention includes a transmitter housing 12 with a generally rectangular configuration. As best shown in FIGS.

2, 3, 4, 5 and 6, the transmitter housing has a first portion 14 and a second portion 16. The first portion includes a top face, a bottom face, and a thin periphery formed therebetween thus defining an interior space. Access is afforded to the interior space via an open side face 18. The first portion further includes a transparent window 20 formed on the top face with indicia 22 printed adjacent thereto. Such indicia includes a plurality of evenly spaced gauged numbers. A closed coupling loop 24 is formed on a side face of the transmitter housing opposite the open side face. A bottom planar extension 26 is integrally formed with the bottom face and extended outwardly therefrom. The bottom planar extension resides within a plane in which the bottom face resides. The bottom planar extension includes a post 28 coupled thereto. The post extends upwardly therefrom with a bulb 30 formed on a top portion thereof.

With reference still to FIGS. 2 and 3, the second portion of the housing includes a top face with a periphery integrally coupled thereto and depending therefrom. The second portion further includes a top planar extension 32 integrally formed with the top face thereof. The top planar extension is adapted to be slidably inserted within the interior space of the first portion. A plurality of markers 34 are printed on the top planar extension which are visible through the window of the first portion. As such, the markers work in conjunction with the indicia of the first portion for affording visual indication of the depth in which the top planar extension is inserted within the first portion. The second portion further includes a groove 36 formed in the top surface thereof for accepting the post therein. Such a feature maintains a slidable relationship between the first portion and second portion. Also, another closed coupling loop 25 is integrally coupled to the periphery of the second portion opposite the top planar extension thereof. The second portion has an unbiased contracted orientation with the second portion proximally situated with respect to the first portion. The second portion also has a biased extended orientation with the second portion distally situated with respect to the first portion. The bottom planar face ensures that the skin or clothing of the infant is not pinched or chafed by the movement of the first portion and second portion.

Also included is a stiff strap 40 with a first extent 42 having a first end coupled to the coupling loop of the first portion of the housing. A second end of the first extent has a pair of pile fasteners 43 coupled thereto. Ideally, a first pile fastener is sewn adjacent to the second end of the first extent of the strap and a second pile fastener is sewn adjacent thereto. The strap further has a second extent 44 with a first end coupled to the coupling loop of the second portion of the housing. A second end of the second extent has a buckle 45 coupled thereto. The strap thus allows the securement of the transmitter housing to a chest of an infant for allowing the housing to be repeatedly biased coincidently with the breathing of the infant. Ideally, each strap is approximately 11 cm in length.

A conductive strip 46 is situated on the top planar extension of the second portion of the housing. working in conjunction with the strip is a plurality of linearly aligned contacts 48. The contacts are situated within the interior space of the first portion of the housing in linear alignment and in contact with the conductive strip. In operation, a decreasing amount of contacts are connected via the conductive strip upon the sliding of the second portion of the housing from an unbiased orientation to a biased orientation.

Further included is a transmitter subunit 50 situated within the interior space of the first portion of the housing. The transmitter subunit is connected to a small battery 52 and the contacts. The transmitter subunit has a comparator 53 (with adjustment switches) which is adapted to monitor the conductivity between subsequent contacts. Also, the transmitter is adapted to transmit an activation signal upon the detection by the comparator of the strip connecting an amount of contacts greater than a predetermined amount of time. As an option, a pair of pivot switches is situated on the housing and is adapted to selectively increase or decrease the predetermined amount of contacts and the predetermined amount of time mentioned hereinabove.

Finally, as shown in FIG. 7, a receiver 58 includes a housing with a generally rectangular configuration. A speaker 60 located within the receiver housing is adapted to emit an alarm upon the actuation thereof. Optionally, an alarm selection button 62 is adapted to allow the receiver to selectively vibrate in combination with emitting an audible alarm upon the receipt of the activation signal via the transmitter unit. In use, the transmitter housing has a first portion and a second portion, wherein the second portion has an unbiased contracted orientation with the second portion proximally situated with respect to the first portion. The second portion further has a biased extended orientation with the second portion distally situated with respect to the first portion. The strap is included for allowing securement of the transmitter housing to an infant. Such securement allows the housing to be repeatedly biased coincidently with the breathing of the infant. It is imperative that the plurality of linearly aligned contacts be situated within the first portion of the housing in linear alignment with the conductive strip which is situated on the second portion of the housing. By this structure, a decreasing amount of contacts are connected via the conductive strip upon the sliding of the second portion of the housing from the unbiased orientation to the biased orientation thereof or, in other words, an increasing amount of contacts are connected via the conductive strip upon the sliding of the second portion of the housing from the biased orientation to the unbiased orientation thereof. The transmitter unit is connected to a small battery and the contacts such that the transmitter unit is adapted to transmit an activation signal upon the detection of the strip connecting an amount of contacts greater than a predetermined amount for a predetermined amount of time. Since an increasing amount of contacts are connected via the conductive strip upon the sliding of the second portion of the housing from the biased orientation to the unbiased orientation thereof, it is apparent that when an infant stops breathing, the housing will assume the unbiased orientation which means an increased amount of contacts are connected via the conductive strip. This allows the transmitter to transmit an activation signal which, in turn, actuates the receiver.

FIG. 8 illustrates an infant 201 with an alternative embodiment apnea detection present invention device 221. Stiff strap 203 is similar to stiff strap 42 and 44 described above except that it includes auxiliary shoulder straps 205 and 207 with fasteners 209 and 211 for attachment to the infants' shoulders. It also includes an auxiliary torso strap which includes a main section 215 and two sections 223 and 227 as well as a fastener 217 and is connected in the back (not shown) to stiff strap 203. Either shoulder straps 205 and 207 or torso strap 215 may be used separately or together. Preferably, they are used together so as to maintain apnea detection device 221 in a substantially fixed position on infant 201.

Referring to FIG. 9, there is shown a front detailed view of present invention 221. This includes a housing 212 with a first portion 214 and a second portion 216. First portion 214 has an open side face 218 to permit slidable motion of second portion 216 therein. Strap 203 is broken and shows a first end portion 244 with a fastener component 245. The other half of strap 203 is shown as strap 242 with end portion 240 and corresponding fastening means 243. Strap 203 and strap 242 are attached by loops 226 and 224, respectively, to second portion 216 and first portion 214. First portion 214 includes a battery 252 wired to transmitter subunit 250 (wiring not shown for simplicity), which includes a transmitter and a comparator 253. There are a plurality of linearly aligned contacts such as contacts 246 and 248 which are situated inside of first portion 214. Second portion 216 has a top planar extension 232, which operates similarly to top planar extension 32 described in conjunction with the device described with respect to FIGS. 2 through 6 above. Post 228, bulb 230 and groove 236 work in a fashion similar to post 28, bulb 30 and groove 36 described with respect to the above Figures. This embodiment, however, does not include a window or indicia, as visual presentation of positioning is not essential to the functioning of the device. Further, first portion 214 is not rectangular in shape yet its shape is not critical to the functionality of the device. Likewise second portion 216 need not be rectangular and may be of any shape, as long as it is functional.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

Obviously, numerous modifications and variations of the present invention are possible in light of the above teachings. It is therefore understood that within the scope of the appended claims, the invention may be practiced otherwise than as specifically described herein.

What is claimed is:

1. An apnea detection device with a remote monitor comprising, in combination:

a transmitter housing having a first portion and a second portion, the first portion including a top face, a bottom face, and a thin periphery formed therebetween defining an interior space with access afforded thereto via an open side face, the first portion further including an attachment means for attaching a strap thereto, said attachment means being formed on a side face opposite the open side face, and a bottom planar extension integrally formed with the bottom face and extended outwardly therefrom within a plane in which the bottom face resides, the bottom planar extension including a stop coupled thereto and extended upwardly therefrom, the second portion of the housing including a top face with a periphery integrally coupled thereto and depending therefrom, the second portion further including a top planar extension integrally formed with the top face thereof with the top planar extension adapted to be slidably inserted within the interior space of the first portion, the second portion further including a groove formed in the top surface thereof for accepting the stop therein so as to maintain a slidable relationship between the first portion and second portion and another strap attachment means, second means being formed at the second portion opposite the top planar extension thereof, wherein the second portion has an unbiased contracted orientation with the second portion proximally situated with respect to the first portion and a biased extended orientation with the second portion distally situated with respect to the first portion;

a stiff strap with a first extent having a first end connected to the attachment means of the first portion of the housing and a second end with a fastener coupled thereto, the strap further having a second extent with a first end coupled to the attachment means of the second portion of the housing and a second end with a second fastener coupled thereto, said second fastener corresponding to and for connection to said first fastener, whereby the strap allows securement of the housing to a chest of an infant thus allowing the housing to be repeatedly biased coincidently with breathing of the infant;

a conductive strip situated on the top planar extension of the second portion of the housing;

a plurality of linearly aligned contact situated within the interior space of the first portion of the housing in linear alignment and the contact with the conductive strip, whereby a decreasing amount of contacts are connected via the conductive strip upon the sliding of the second portion of the housing from an unbiased orientation to a biased orientation;

a transmitter subunit situated within the interior space of the first portion of the housing and connected to a small battery and the contacts, the transmitter subunit including a comparator which is adapted to monitor the conductivity between subsequent contacts and a transmitter adapted to transmit an activation signal upon the detection by said comparator of the strip connecting an amount of contacts less than a predetermined amount; and, a remote receiver including a housing with a speaker adapted to emit an alarm upon the actuation thereof, a power source and a receiver unit adapted to actuate the speaker upon the receipt of the activation signal via the transmitter unit.

2. The device of claim 1 wherein said stiff strap further includes two auxiliary shoulder straps to extend at approximately right angles therefrom with opening and fastening means and each being connected at a front portion and a back portion of said stiff strap so as to be attachable over the shoulders' of an infant.

3. The device of claim 1 further including an auxiliary torso strap, said auxiliary torso strap, being connected to said stiff strap at a front portion and a back portion with opening and fastening means and adapted to be fastened about the crotch area of an infant.

4. The device of claim 2 further including an auxiliary torso strap, said auxiliary torso strap, being connected to said stiff strap at a front portion and a back portion with opening and fastening means and adapted to be fastened about the crotch area of an infant.

5. The device of claim 1 wherein said device further includes a pair of switches situated on the housing adapted to selectively increase or decrease the predetermined amount of contacts and the predetermined amount of time.

6. The device of claim 1 wherein includes a plurality of receivers which includes a housing with a speaker adapted to emit an alarm upon the actuation thereof, a power source and a receiver unit adapted to actuate the speaker upon the receipt of the activation signal via the transmitter unit.

7. The device of claim 2 wherein includes a plurality of receivers which includes a housing with a speaker adapted to emit an alarm upon the actuation thereof, a power source and a receiver unit adapted to actuate the speaker upon the receipt of the activation signal via the transmitter unit.

8. The device of claim 3 wherein includes a plurality of receivers which includes a housing with a speaker adapted to emit an alarm upon the actuation thereof, a power source and a receiver unit adapted to actuate the speaker upon the receipt of the activation signal via the transmitter unit.

9. The device of claim 4 wherein includes a plurality of receivers which includes a housing with a speaker adapted to emit an alarm upon the actuation thereof, a power source and a receiver unit adapted to actuate the speaker upon the receipt of the activation signal via the transmitter unit.

10. The device of claim 5 wherein includes a plurality of receivers which includes a housing with a speaker adapted to emit an alarm upon the actuation thereof, a power source and a receiver unit adapted to actuate the speaker upon the receipt of the activation signal via the transmitter unit.

11. The device of claim 1 wherein said power source is a battery power source.

12. The device of claim 6 wherein said power source is a battery power source.

13. The device of claim 1 wherein said power source is a line-in plug for household power.

14. The device of claim 6 wherein said power source is a line-in plug for household power.

\* \* \* \* \*